United States Patent [19]

Krieger

[11] Patent Number: 5,728,172

[45] Date of Patent: Mar. 17, 1998

[54] HINGE JOINT IN ORTHOPAEDIC PROSTHESES AND ORTHESES

[75] Inventor: Wilfried Krieger, Göttingen, Germany

[73] Assignee: Otto Bock Orthopadische Industrie Besitz-und Verwaltungs KG, Germany

[21] Appl. No.: 496,717

[22] Filed: Jun. 29, 1995

Related U.S. Application Data

[63] Continuation of Ser. No. 128,594, Sep. 28, 1993, abandoned.

[30] Foreign Application Priority Data

Sep. 29, 1992 [DE] Germany ............... 42 32 602.8

[51] Int. Cl.$^6$ ..................................................... A61F 2/64
[52] U.S. Cl. ............................. 623/44; 623/39; 623/45; 602/26
[58] Field of Search ........................... 623/39, 44, 46, 623/40–43, 45; 602/16, 26

[56] References Cited

U.S. PATENT DOCUMENTS

| | | | |
|---|---|---|---|
| 2,175,136 | 5/1939 | Stewart | 623/46 |
| 3,673,613 | 7/1972 | Asbelle et al. | 623/45 |
| 4,090,264 | 5/1978 | Thompson | 623/44 |
| 4,145,766 | 3/1979 | May | 623/45 |
| 4,179,759 | 12/1979 | Smith | 623/42 |
| 4,911,709 | 3/1990 | Marlow et al. | 623/39 |
| 5,020,790 | 6/1991 | Beard et al. | 602/16 |
| 5,171,325 | 12/1992 | Aulie | 623/39 |
| 5,181,931 | 1/1993 | vande Veen | 623/46 |
| 5,201,776 | 4/1993 | Freeman | 602/26 |
| 5,376,137 | 12/1994 | Shorter et al. | 623/46 |

FOREIGN PATENT DOCUMENTS

| | | | |
|---|---|---|---|
| 2056281 | 3/1981 | United Kingdom | 623/44 |
| 9222267 | 12/1992 | WIPO | 623/44 |

Primary Examiner—John G. Weiss
Assistant Examiner—Bruce Snow
Attorney, Agent, or Firm—Bachman & LaPointe, P.C.

[57] ABSTRACT

The invention relates to a hinge joint or swivel coupling in orthopaedic prosthesis and ortheses, with an upper joint component (1), a lower joint component (2) and, if applicable, interposed control arms (9, 10) (hereinafter designated collectively as "hinge joint members") and a control element (4), that effectively engages both sides of a hinge joint member (1; 1, 2) (hereinafter "articulated joint member") each via one hinge point (7, 8) distanced from a pivot (3; 20, 21; 25, 26). To effect an improvement, the invention proposes that at least one of the above-mentioned hinge points (7, 8) is kinematically connected to at least one other hinge joint member (2; 9, 10; 9) via a mechanical geared coupling (11, 12, 13, 14; 15, 16, 17; 18, 24; 30, 31) and is arranged in such a way that it can change position in relation to its articulated joint member (1; 1, 2). FIG. 17.

6 Claims, 14 Drawing Sheets

HINGE JOINT IN ORTHOPAEDIC PROSTHESES AND ORTHESES

This is a continuation of application Ser. No. 08/128,594 filed on Sep. 28, 1993 now abandoned.

BACKGROUND OF THE INVENTION

The invention relates to a hinge joint or swivel coupling in orthopaedic prosthesis and ortheses, with an upper joint component, a lower joint component and, if applicable, interposed control arms (hereinafter designated collectively as "hinge joint members") and a control element, that effectively engages both sides of a hinge joint member (hereinafter "articulated joint member") each via one hinge point distanced from a pivot.

This hinge joint can, for example, be a unicentered or polycentred prosthetic knee joint, in which case the individual configuration of the hinge joint members does not matter.

In the invention it is irrelevant whether the control elements or control systems affect a single hinge joint or single swivel coupling, or whether they affect several hinge joints or swivel couplings simultaneously.

The control of the movement of the hinge joints in orthopaedic prostheses and ortheses is only accomplished in a limited way in the known embodiments. This is primarily due to the fact that the control of movement is passive in many instances. The technical operating elements can in these cases not act themselves, for example, generate movement themselves, but are generally limited to react passively to movements, which they affect with movement resisting and/or springloaded cushioning systems. This applies typically to the hinge joints in orthopaedic leg prostheses. Thus, for example, in known prosthetic knee joints it is preferred to use movement resisting and/or springloaded cushioning systems which either counter basically every joint movement or specifically support individual joint movements through the use of previously stored energy. A known example for a springloaded cushioning operating element is the elastic orthopaedic knee strap formerly widely used in conventional knee-shin-assemblies, which is fixed to the upper and shin of the prosthesis and thus bridges the knee joint at the front. It is increasingly tensioned when a knee bend is started from the pretensioned stretch position. As a result, it counters the movement of the knee and supports the return movement to the stretch position. This operating element suffers from a major defect, however: the knee stretch moment resulting from the strap effect increases continuously as the knee bend angle becomes greater. For this reason, assuming a sitting position without difficulty, whereby the prosthetic knee joint is at a bend angle approaching 90°, is limited without additional technical devices, because in this body position the largely unloaded prosthetic shin is attempting to return to its stretch position.

In modern orthopaedic prostheses and ortheses, control elements and control systems are used to control the hinge joints, which are placed between individual hinge joint members in such a way that the distance between their hinge points changes depending on the joint movement or rotation. Such control elements are known, for example, in elbow joints, ankle, knee and hip joints of leg prostheses, in hand joint and elbow areas of orthopaedic arm ortheses, or in ankle, knee and hip joints of orthopaedic leg ortheses.

Most common are the control elements of known art, however, in unicentered and polycentred knee joints of orthopaedic leg prostheses. For that reason, these uses are most often referred to in the embodiments described below. In this case, the control elements are used to enhance the knee security of the stretched prosthesis during the standing phase of the forward motion, in which the prosthesis supports the body and/or the control of movement of the prosthesis shin in the swing phase, during which the shin swings back and forth in a pendulum fashion, while the other leg supports the body.

The purpose of the invention is to provide a hinge joint of the embodiment described above with improved properties.

In connection with the hinge joint characteristics described at the beginning, this purpose is accomplished by the invention, by means of having at least one of the above-mentioned hinge points is kinematically connected to at least one other hinge joint member via a mechanical geared coupling and is arranged in such a way that it can change position in relation to its articulated joint member.

Thereby the positional change of at least one of the hinge points can be a circular path around an axis of rotation intended around one of the articulated joint members; the change in position can, however, also be a sliding movement along a predetermined slide path.

The mechanical geared coupling may be a spur gear drive, which is designed with a single stage or with several, whereby one stage may be composed of a pinion gear drive or of a friction gear. The gear wheels of one stage of the drive may be designed as a meshing or rolling cam gear drive. Other variations are contained in the patent subclaims and will be explained using further examples of embodiments.

The change in position of at least one hinge point in relation to its articulated joint member can take place along a path which may be designed freely, properly using all feasible technical variations of drives according to the desired effect of each. In that way, the designer is, for the first time, offered the opportunity to optimize several individual functions independently from each other.

In essence, the direct and indirect effects of the change in position in accordance with the invention, on individual functional characteristics of the hinge joints described, may be distinguished from each other:

There is a direct effect in accordance with the invention on, for example, the dimension and progression of the effective complete lever arm of the articulation relating to the action of force of the control element on the fulcrum point of a unicentered hinge point or the instantaneous center of the movement of a polycentered hinge joint. The dimension and progression of the stroke of a control element as well as the position of the action reversal, are also directly affected.

The articulation moments from the action of a movement-resisting control element which functions on the mechanical friction principle are affected indirectly. The same applies to the articulation moments from the action of a springloaded cushioning control element, as well as from the action of a movement-resisting control element whose action depends on the speed of its translatory motion (this particularly includes fluid damping units).

The indirect effect of the change in position of the articulation in accordance with the invention on the last-named type of control elements is shown in the following:

The stroke at the control element as a directly affected dimension is kinematically dependent on the angular movement of the hinge joint in question. For certain types of movements of human extremities the angular movements are dependent upon time, e.g. they display a characteristic angular velocity profile. Control elements of the fluid damping units types which are used in one and the same type of a hinge joint of an orthopaedic aid, for example in the knee joint of a leg prosthesis, in order to imitate the natural angular movement as closely as possible, have shown in practice that they can only meet this requirement at predetermined angular velocity profiles of the hinge joint when the speed of their piston rods is also high enough at the same time. For that purpose, it requires a minimum stroke which can barely be achieved in the conventional designs when other functional demands are made simultaneously. Through specific application of the concept of joint-angle-dependent change of position of the articulation in accordance with the invention, it is possible, through the increase in the stroke and modification of the stroke progression as the direct influence factor, to enhance the stroke velocity in the desired manner at the same time in an indirect manner.

A unicentered prosthetic knee joint in accordance with the invention can be characterized by the fact that the lower joint component is securely attached to a primary spur gear co-axially arranged on the joint pivot; this spur gear engages a second spur gear which is mounted rotatably on the upper joint component with its axis of rotation in alignment with the pivot in front of (stretching side) or behind (bending side) it and is fitted with a crank arm, to which the control element is hinged via at least one hinge point.

A polycentered prosthetic knee joint in the form of a four-member kinematic joint link chain, in which the upper joint component is coupled to the lower joint component via a front (stretching side) and a rear (bending side) articulation, can, in accordance with the invention, be designed in such a way that the front control arm is coupled co-axially to its top joint pivot, which connects it with the upper joint component, and a first spur gear so that it cannot turn; this spur gear engages a second spur gear which is rotatably mounted on the upper joint pivot which connects the rear articulation with the upper joint component and is fitted with a crank arm to which the control element is hinged via at least one hinge point.

Other characteristics of the invention are contained in the subclaims and will be explained in detail in relation to further advantages of the invention using examples of embodiments.

The drawings illustrate several forms of embodiments serving as examples, as well as examples showing the known state of the art. These are:

In order to better understand matters, the problem forming the basis for the invention is discussed in more detail with reference to the state of the art:

DETAILED DESCRIPTION OF THE PREFERRED EMBODIMENTS

Figure 18A:
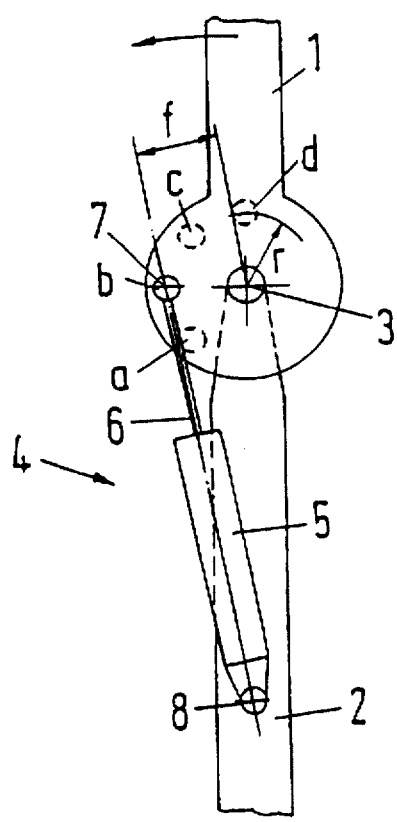
FIG. 18—a schematic illustration of the state of the art articulation of a control element designed as a cylinder with a piston rod in fixed articulation position in a unicentered hinge joint.
Figure 18B:
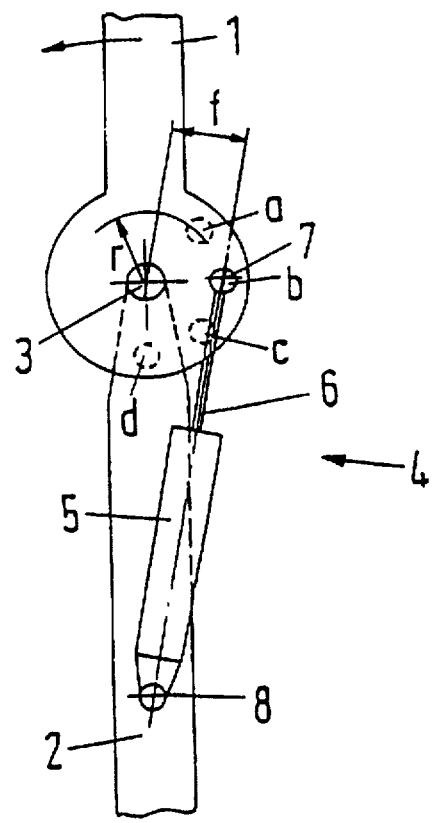

FIG. 18 shows in illustration A at left and in illustration B at right, a hinge joint or a swivel coupling consisting of an upper joint component 1, a lower joint component 2 and the pivot 3 connecting the two parts 1,2 allowing them to swivel, which is fixed securely to the lower joint component 2. This is a unicentered hinge joint or a unicentered swivel coupling, illustrated in the stretched position. It is further provided with a control element 4 which consists of a cylinder 5 with a piston rod 6 in both examples of the embodiment. This control element 4, which changes length, is hinged at its top to upper joint component 1 and at its lower end to the lower joint component 2. The upper hinge point is here designated by 7 and the lower pivotal point by 8.

In the illustration A at left, the upper hinge point 7 is at the bending side of the joint and thus behind its pivot 3, the right illustration B, however, is at the stretching side of the joint and thus in front of the pivot 3. The control element 4 is with its longitudinal axis almost completely along the bending side in illustration A at left, but on the stretching side in illustration B at right. For that reason, the start of a bend of the joint, for example, by pivoting of the upper joint component 1 in the direction of the arrow to the rear in an embodiment in accordance with A, results in a reduction of the distance between the two hinge points 7, 8, namely to an inwards movement of piston rod 6 into cylinder 5, while the identical bend in embodiment B results in an increase of the distance between the hinge points 7, 8 and thus to an outwards movement of piston rod 6 out of cylinder 5.

The position of the upper hinge point 7 on upper joint component 1 in relation to the pivot 3 determines whether the pivoting side of control element 4 under continued bending movement of the joint changes in an area where its design allows, that is, whether the longitudinal axis of control element 4 in the embodiment in accordance with A moves from a position behind the pivot 3 to a position in front of this pivot 3, or whether the longitudinal axis of control element 4 in an embodiment in accordance with B moves from a position in front of the pivot 3 to a position behind this pivot 3. When such a change occurs, then the translatory motion of piston rod 6 to cylinder 5 reverses simultaneously and thus also the direction of its action starting from this position to the previous state of rest or previous zero passage (hereafter designated as action reversal or "WU"). This may lead to various effects on the hinge joint depending on the operation of the control element 4: a springloaded cushioning system which counters the joint movement until the WU boundary is reached, will support this joint movement after the WU boundary has been crossed. The opposite sequence of actions is naturally also possible.

A movement-resisting system can after crossing the WU boundary also exert various effects on the hinge joint: with operation in both directions of motion, this movement-resisting system (control element) will counteract the joint movement, using variable resistance characteristics as applicable. When operating in only one direction of motion, the control element becomes ineffective, whereby, as in the case of a springloaded cushioning system, the reverse sequence of actions is also possible in this case.

This action reversal starts at various bending angles, depending on the position of the upper hinge point 7 on the upper joint component 1 (in relation to the pivot 3), and actually whenever the longitudinal axis of control element 4 cuts across the pivot 3. This occurs with the four upper hinge points a, b, c and d drawn in the two embodiments A and B nearly uniformly at the following bending angles: 45° for a, 90° for b, 135° for c and 180° for d. In the case of, unicentered prosthetic knee joints, the only hinging options of practical significance for control elements 4 pivoting at the bending and stretching sides are hinging variations b and c, whereby variation b is generally preferred because of the action reversal at approximately 90°. That is because if cylinder 5 has a springloaded element fitted which is tensioned when a movement of the joint is initiated from the stretch position, then its action reversal at a bending angle of approximately 90° will ease sitting by the amputee, because the stretching effect of the tensioned springloaded element on the lower thigh at this angle is exactly zero and this reverses when the angle is exceeded, i.e. supporting the bending position.

Hinging variation b nevertheless has some serious disadvantages: the position of the upper hinge point 7 relating to the pivot 3 is also a decisive factor on the dimension and progression of the translatory motion of piston rod 6 compared to cylinder 5 depending on the bending angle of the hinge joint. Furthermore, the aforementioned position determines the progression of the perpendicular distance f of the longitudinal axis of control element 4 to the pivot 3 depending on the bending angle of the hinge joint. This distance f is the dimension for the effective lever arm, to which the forces between control element 4 and hinge joint are transferred and act, for example, as knee momentum.

If one assumes, based on the two examples of an embodiment in FIG. 18, that the four hinge points a to d considered to be possible are arranged on a sector with the radius r around the pivot 3, then FIG. 18 shows immediately that within a joint bending range of 0° to 180° the maximum value of the translatory motion of the piston rod 6 to cylinder 5 designated as stroke (H) cannot exceed the double value of the articulation radius r and the maximum value of the effective lever arm f cannot exceed the single value of the articulation radius r. The decisive factors for the effect of the control elements or control systems are thus stroke H and effective lever arm f which up until now have set relatively tight movement limits for the designer of endoskeletal prosthetic components.

Figure 19:
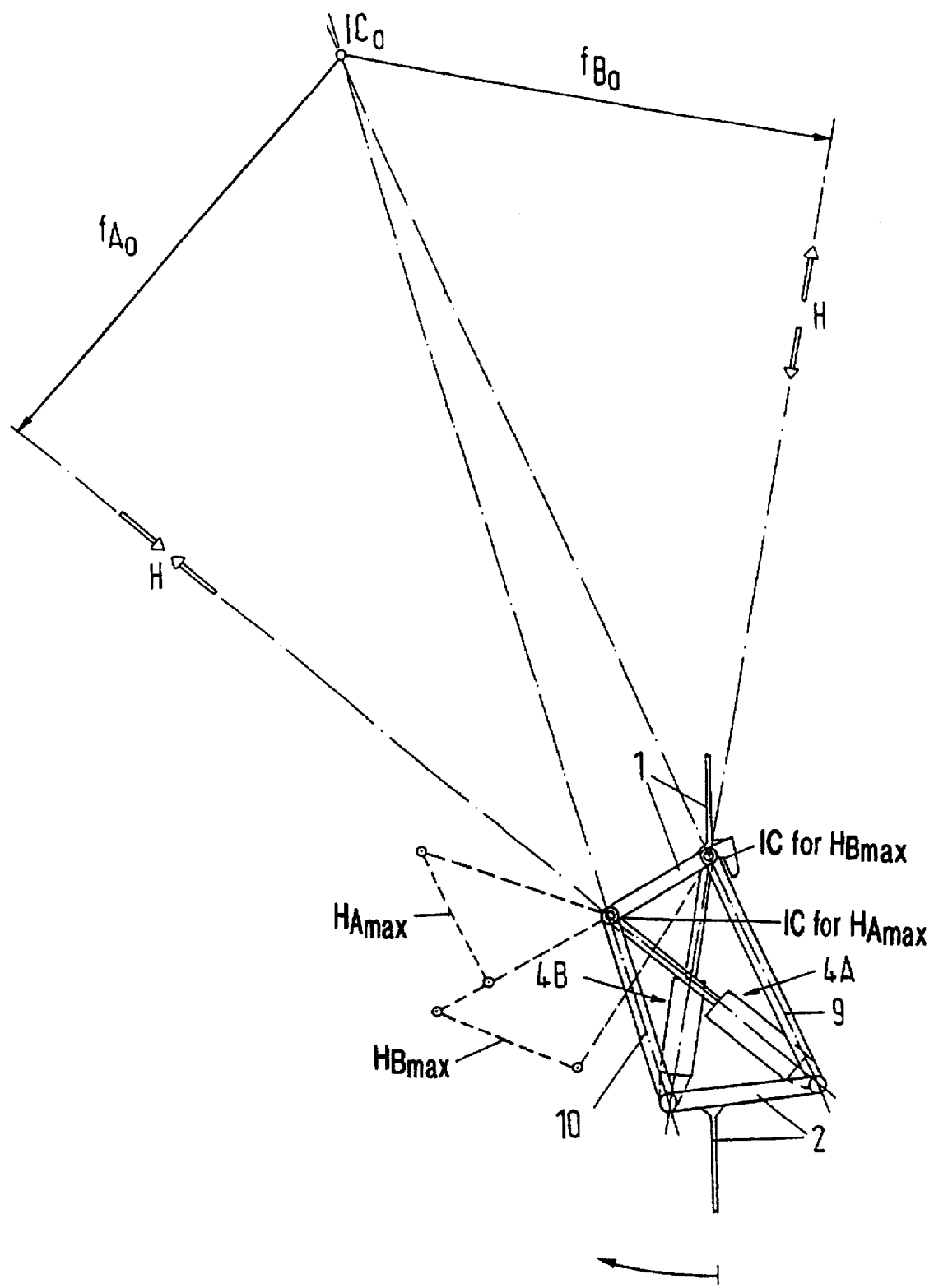
FIG. 19—an illustration as in FIG. 4 of the state of the art of a polycentered hinge joint with two fixed articulated diagonal control elements each consisting of a cylinder with a piston rod.

The state of the art as shown in FIG. 19 for a polycentered hinge joint or a polycentered swivel coupling in the form of a four-member kinematic link chain in which the upper joint component 1 is coupled to the lower joint component 2 via a front (stretched side) linkage arm 9 and a rear linkage arm 10 (bending side). Also shown are two different, diagonally hinged control elements 4A and 4B, which are a direct and immediate hinge between two adjacent members of a joint. Herein the arrangement of the control element 4A corresponds nearly to a knee exoarticulation hinge joint in accordance with DE 28 41 999 C2. Regarding the relative motions between cylinder and piston rod at the commencement of a bending movement of the joint from the stretched position, the corresponding previous explanations given for FIG. 18 apply, with the difference that it is not the position of the longitudinal axis of control element 4 shown as connecting in a straight line through its hinge points to the pivot, but rather the instantaneous center (IC) of the movement of the hinge joint that is decisive for the direction of these relative motions.

Both the configuration with control element 4A and the one with control element 4B exhibit deficiencies from several points of view: the maximum value of the effective lever arm f already occurs in the stretched position. The maximum stroke $H_{max}$ is not very great. When used in a prosthetic knee joint, the action reversal occurs in configuration B at about 30° and in configuration A at about 70°, thus too early, that is, at too small a bending angle.

Figure 1A:
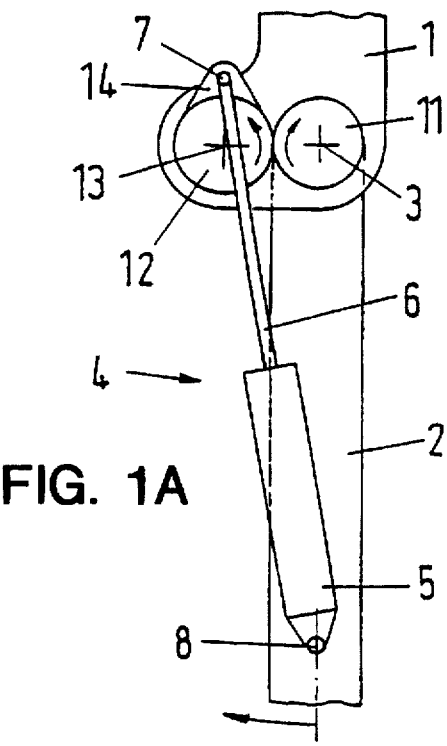
FIG. 1—a schematic illustration of a bending and stretching side of an upper articulation of a control element designed as a cylinder with piston rod in a unicentered joint using a single-stage spur gear drive.
Figure 1B:
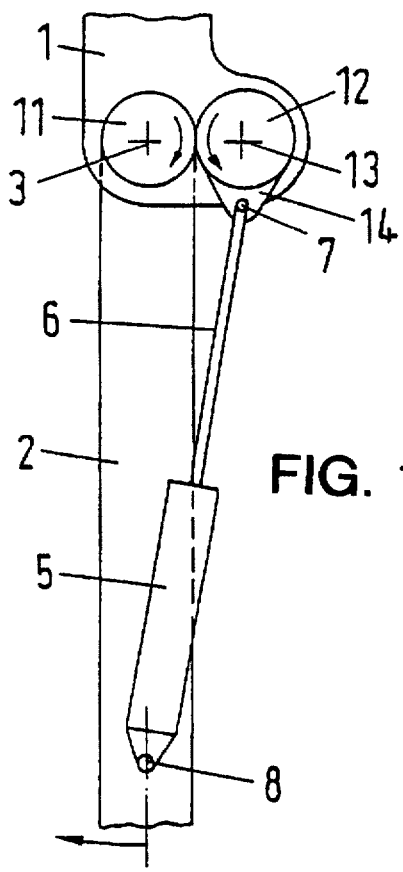

In order to solve the above-mentioned problems associated with the current state of the art, the following examples of embodiments of the invention are described:

FIG. 1 shows illustrations similar to FIG. 18. Again, two unicentered joints are shown with each an upper joint component 1, a lower joint component 2, a pivot 3 and a control element 4, which again is formed by a cylinder 5 and a piston rod 6. In the left illustration A, the control element is arranged at the bending side, similar to FIG. 18A and in the illustration B at right it is arranged at the stretching side. The upper hinge point of the control element 4 is again designated as item 7 and the lower hinge point as item 8.

However, in accordance with the invention, the upper hinge point 7 is arranged to allow it to alter position compared to upper joint component 1 (articulated joint member) and connected kinematically via a mechanical geared coupling with lower joint component 2. In FIG. 1, the mechanical geared coupling is executed as a single-stage spur gear drive, in which the first spur gear 11 is fixed securely on the pivot 3 which is attached permanently to the lower joint component 2 and engages a second spur gear 12, which is mounted on another pivot 13 so that it can freely rotate on upper joint component 1 and is fitted with a crank arm 14, on which the control element 4 pivots via its upper hinge point 7. In the illustration A at left, the pivot 13 for the second spur gear 12 is behind the pivot 3 and in embodiment B it is in front of pivot 3.

During a bending movement of the lower joint component 2 in the direction of the arrow, the second spur gear 12 performs a rotating motion that is always counter to this bending movement. The upper hinge point 7 of control element 4 then carries out a turning movement along a circular path with nearly equal portions downwards and to the rear and that rotates around the pivot 3, which contributes to the decrease in the distance between the two hinge points 7, 8 of control element 4 and thus to an increase in the stroke of control element 4, when a knee bend is started from the stretched position. The slew angle attained thus is solely dependent on the gear ratio of the spur gear set 11, 12 and is thus freely selectable as is the pivoting radius of the crank arm 14.

Figure 2:
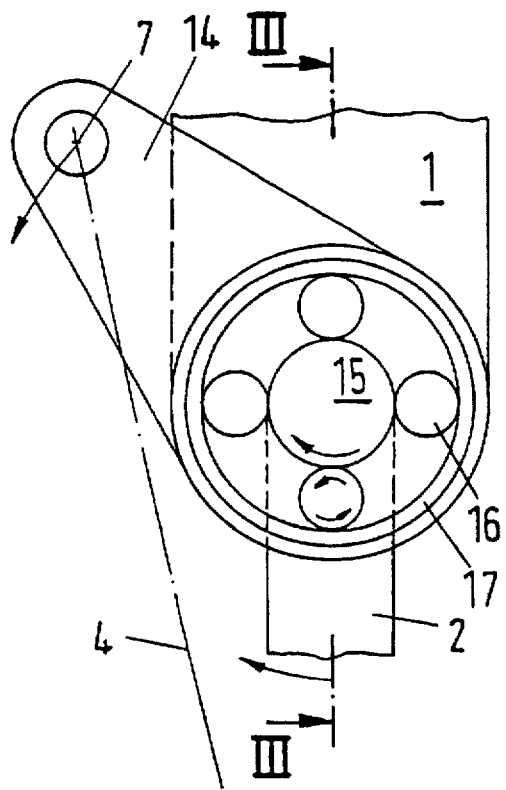
FIG. 2—a top view of a bending-side upper articulation of a control element (not further illustrated) in a unicentered joint using a planetary gear drive.
Figure 3:
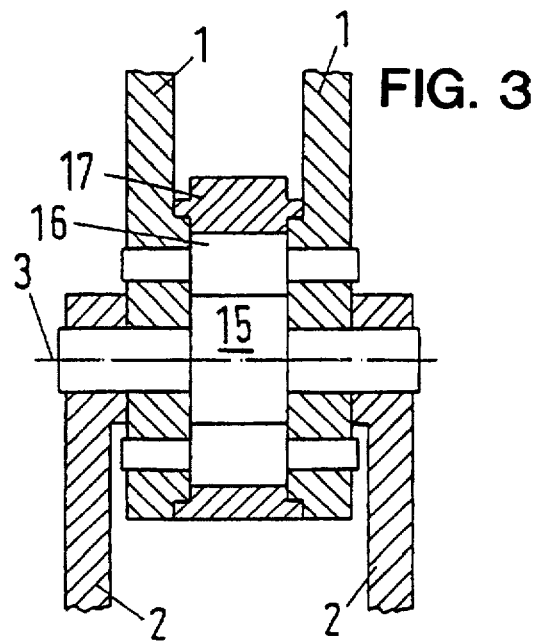
FIG. 3—a cross-section through line III—III in FIG. 2.
Figure 4:
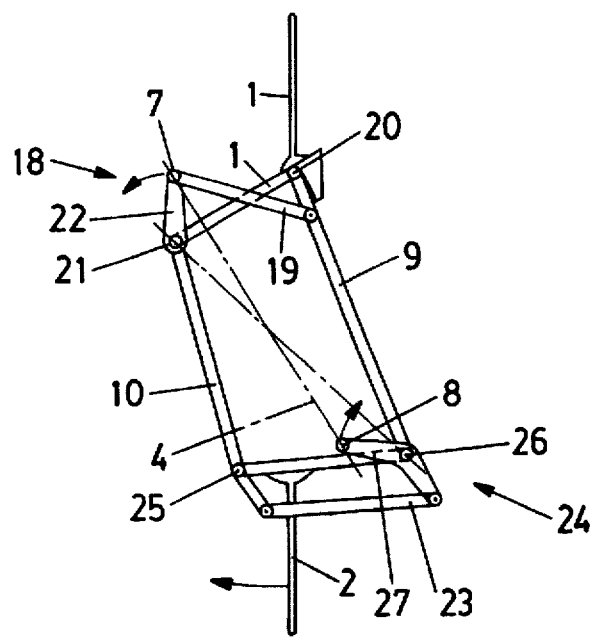
FIG. 4—a schematic illustration of a polycentred prosthetic knee joint, designed as a four-member kinematic link chain, with a diagonal control element articulated via two double crank assemblies.

In the example of an embodiment in accordance with FIG. 2, the mechanical geared coupling between hinge point 7 and the lower joint component 2 in accordance with the invention is achieved by a planetary drive mounted co-axially to pivot 3, whereby the central sun gear 15 is connected to lower joint component 2 and the pinion cage 16 to upper joint component 1. In this arrangement, the planetary ring gear 17 performs a rotary motion that is always opposite to the bending movement of lower joint component 2. The crank arm 14 connected to the planetary ring gear 17 has the upper hinge point 7 for control element 4 at its extremity. During the above-mentioned bending movement, this upper hinge point 7 describes a rotary motion along a slightly rearwards and mostly downwards projected arc, concentric to pivot 3, which contributes to the reduction of the distance between the two hinge points of control element 4 when a bending movement is started from the stretched position and thus also contributes to an increase of the stroke at the control element. The angle of traverse attained thus is solely dependent on the gear ratio between the annular gear 17 and sun gear 15 and is thus as freely selectable as is the pivoting radius of the lever arm 4. FIG. 4 shows the modified arrangement, in accordance with the invention, of the state of the art polycentered joint shown in FIG. 19, consisting of a four-member link chain composed of the upper joint member 1, the lower joint member 2, the front linkage arm 9 and the rear linkage arms 10. The diagonally suspended control element 4 between the upper hinge point 7 and the lower hinge point 8 is only indicated by a dotted line. The longitudinal axis of the control element 4 runs nearly diagonally from the top rear to the bottom front. The swivelling takes place via a double crank assembly. The upper crank assembly 18 pivots at the front linkage arm 9 via its connecting rod 19 underneath the front lower joint 20 of the basic mechanical assembly and drives a lever 22 attached co-axially to the upper rear joint of the basic mechanical assembly via a hinge joint to which the upper hinge point 7 of control element 4 is fixed co-axially.

The connecting rod 23 of the lower double crank assembly is underneath the lower rear joint 25 of the basic mechanical assembly and is hinged to the rear control arm, which is extended downwards, and drives a bell crank 27 which is mounted co-axially to the lower front joint 26 of the basic mechanical assembly, and on whose other end the lower hinge point 8 of control element 4 is located.

For comparison purposes, FIG. 4 also contains the control element 4A, illustrated in the state of the art shown in FIG. 19, and drawn in dotted lines.

Figure 5:
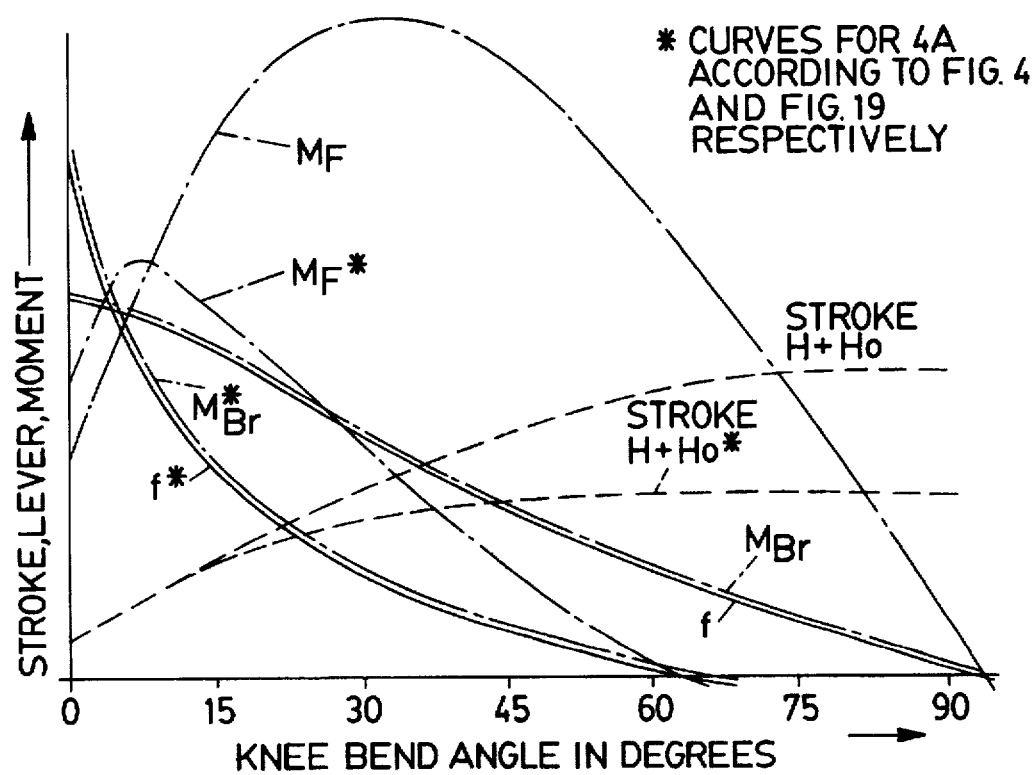
FIG. 5—the progression of the stroke of the control element in FIG. 4, with the effective lever arm and the articulation moment dependent on the knee bend angle.

The progression of the stroke, lift and momentum are represented in FIG. 5 using a knee bend angle from a knee joint as shown in FIG. 4. FIG. 5 clearly shows that all values given are clearly better when compared to the curves drawn for a known joint in accordance with FIG. 19. The action reversal is shifted from a bending position of about 60°, which is much too small for a prosthetic knee joint, to a useful bending position of about 90°. The mathematically effective complete lever arm shows a much better progression. Stroke H is considerably enhanced compared to the reference value and shows an effective progression at the maximum value for the bending of the joint of about 90°. Moment $M_F$ from the action of a springloaded element 4 is considerably strengthened over the entire bending range as a result of the increase in the stroke at greater bending angles, as well as better progression of the mathematically effective complete lever arm and attains its maximum clearly later than the evidently poorly progressing reference value. Moment $M_B$, from the action of a movement-resisting element follows—proportionally dependent—the progression of the mathematically effective complete lever arm. The corresponding embodiments, therefore, apply generally.

To have a better overview of the many possibilities relating to the pivoting of the control element it is useful, to make a differentiation in the individual path characteristics for the path of the upper hinge point of a control element compared to the articulated joint member. For this purpose, the orientation of the orthopaedic technical aid along the longitudinal axis, can be used, particularly those orthopaedic prostheses or ortheses in which the concept of change of position of the pivoting of control elements in accordance with the invention can be employed, generally exhibit a longitudinal axis related to their basic or starting position within the human support and movement device. If one follows this orientation, then a cartesian system of coordinates would be suitable in which the ordinate is designated by L (longitudinal axis) and the abscissa by $Q_{BE}$ (lateral axis in the plane of motion). The positive L-axis points upwards, the positive $Q_{BE}$-axis towards the stretched side of the joint. For unicentered types of joints the origin of the coordinates is set at the joint center and for polycentered joints at a suitable reference point (e.g. the center of one of several prominent pivots).

When arranging for the design or evaluation of the path of the change of position that is dependent on the hinge joint angle, in accordance with the invention, of the pivoting of control elements in joints of orthopaedic prostheses and ortheses in this reference system, it is relatively simple to determine, for a given set of functional requirements, the most effective path of the pivoting depending on the joint angle, either using actions in the L or $Q_{BE}$ direction, or to arrange the L or $Q_{BE}$ components running parallel and laterally to their longitudinal axis along known paths of individual actions, or to relate these to specific path components.

Figure 6:
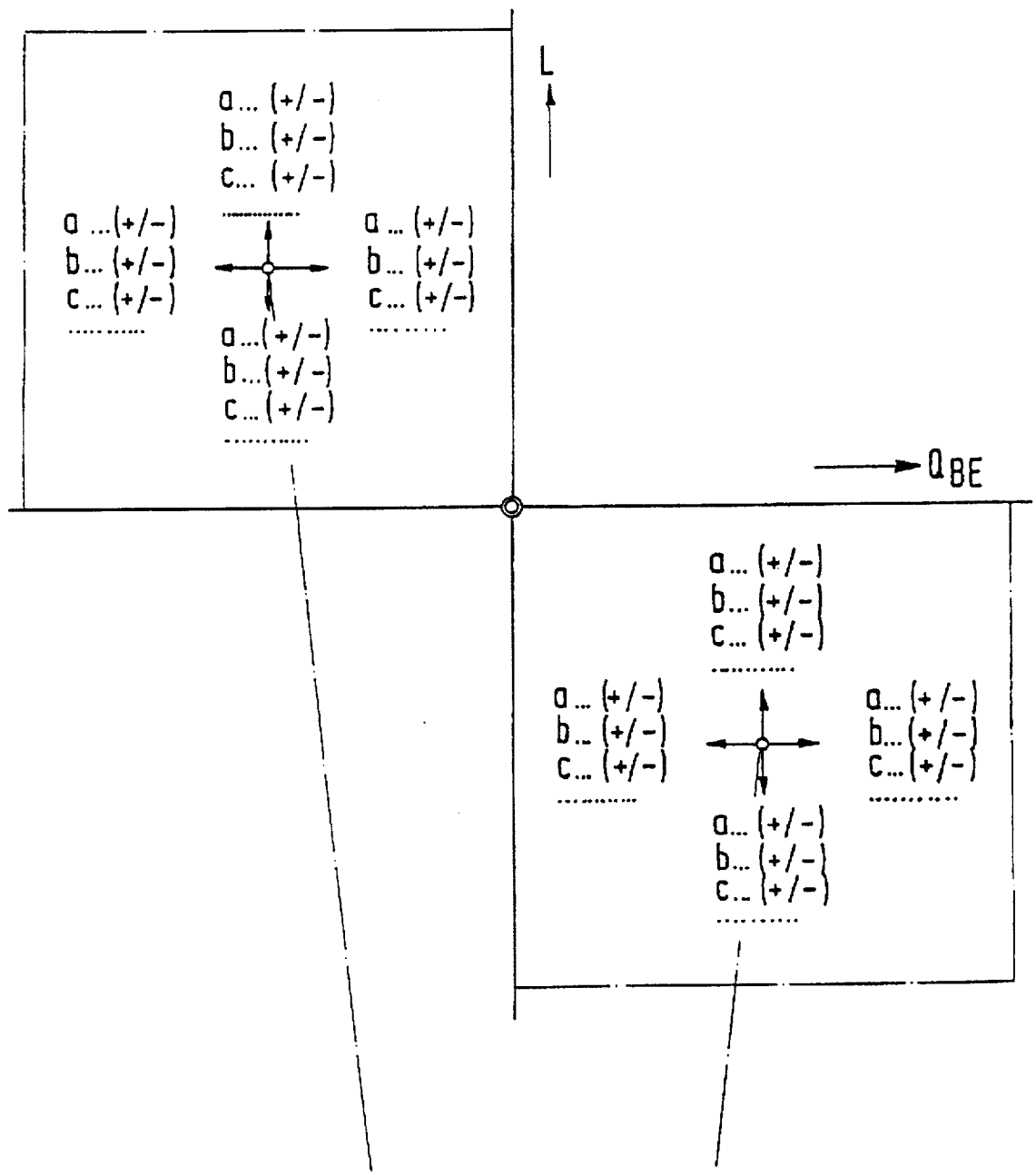
FIG. 6—a general diagram for the application of the concept in accordance with the invention.
Figure 7:
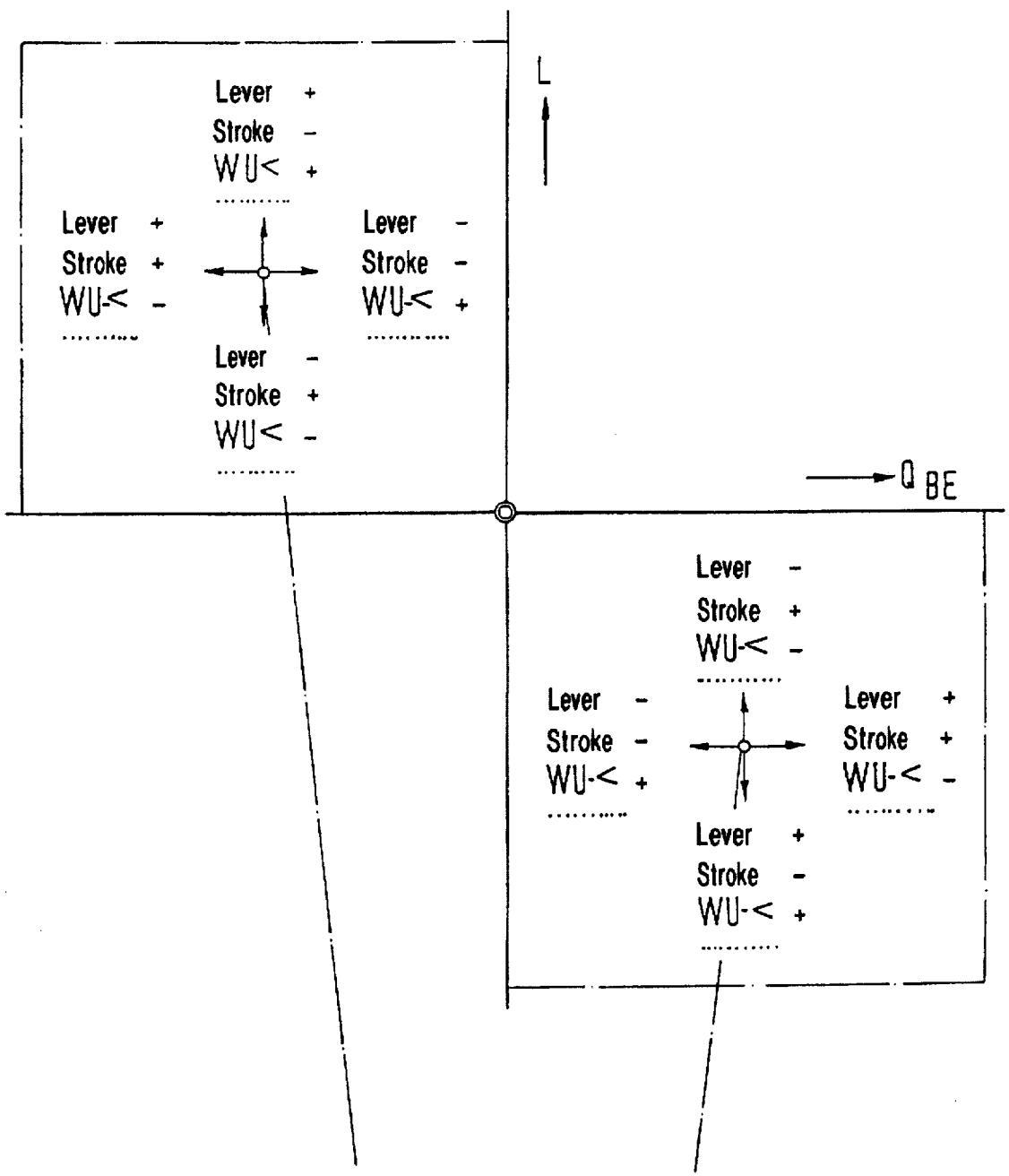
FIG. 7—a diagram as in FIG. 6 with examples of actions with bending and stretching-sided upper articulation of a control element.

This is illustrated in FIG. 6 in a general way and in FIG. 7 specifically, using as an example the upper articulation at the bending and stretching sides for a unicentered prosthetic knee joint which is not further illustrated. In both cases, the hinge points are each arranged in typical quadrants. The same relationships apply to prosthetic hip joints. The illustrations show which actions are achievable individually or in combination, when the hinge point being observed moves, dependent on the joint movement, along the desired or predetermined path of the change of position when a knee bend commences from the stretched position.

Figure 8:
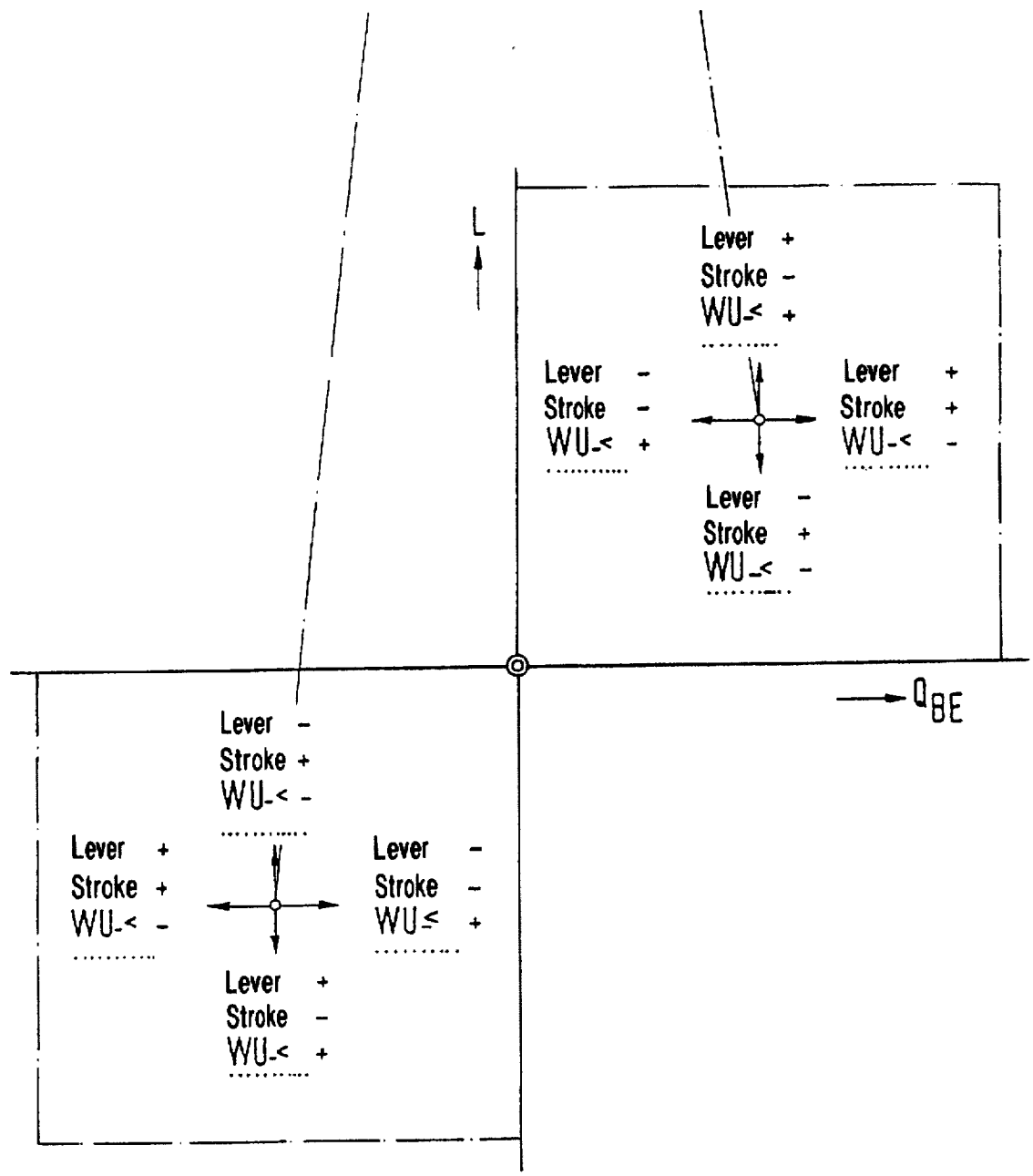
FIG. 8 an illustration as in FIG. 7 for a bending and stretching-side lower articulation of a control element.

For the sake of completeness, the relationships for the upper articulation at the bending and stretching side of a control joint in a unicentered prosthetic knee joint that is not further illustrated in FIG. 7, have been repeated in FIG. 8 for the lower articulation at the bending and stretching side.

Figure 9:
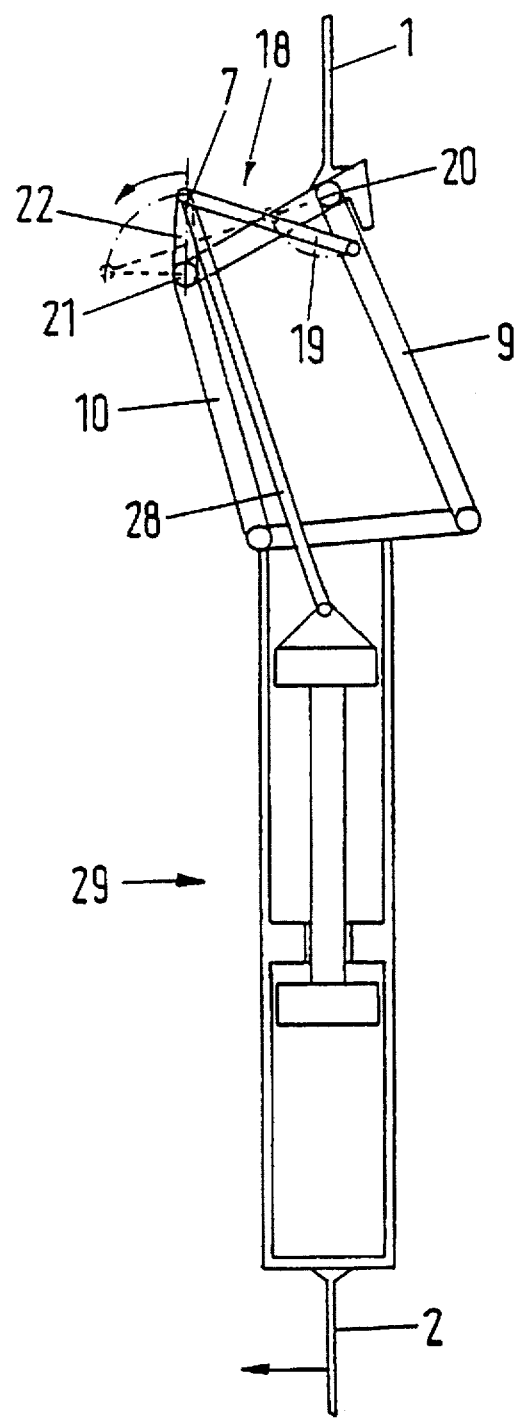
FIG. 9—a schematic illustration of an upper articulation of a connecting rod of a fluid at the bending side, designed as a double sliding piston drive in a polycentered hinge joint using a twin crank assembly.

The following figures show further examples of embodiments in accordance with the invention:

FIG. 9 shows a polycentered joint with an upper double crank assembly 18 in accordance with FIG. 4. At the upper hinge point 7, connecting rod 28 pivots at the bending side of a fluid damping units 29 formed by a double sliding piston drive.

Figure 10:
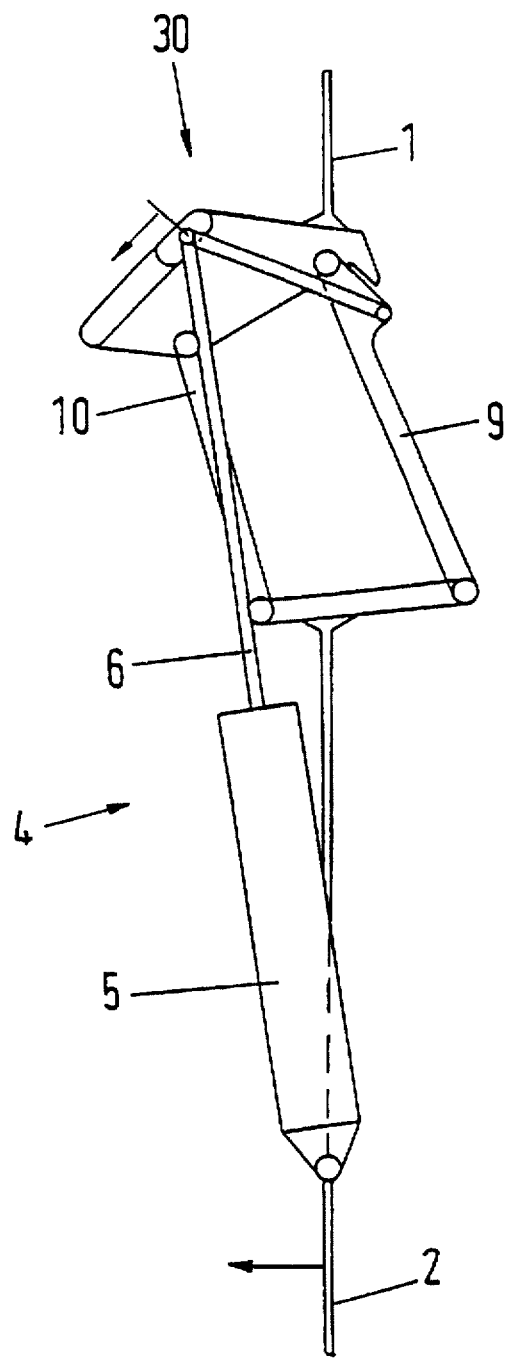
FIG. 10—an illustration as in FIG. 9 of an upper articulation of a control element at the bending side, designed as a cylinder with a piston rod in a polycentered hinge joint using a sliding crank assembly with an external thrust member.

FIG. 10 shows the change in position depending on joint angle of the upper articulation at the bending side of a control element 4 in a polycentered joint using a sliding crank assembly 30 with external thrust member.

Figure 11:
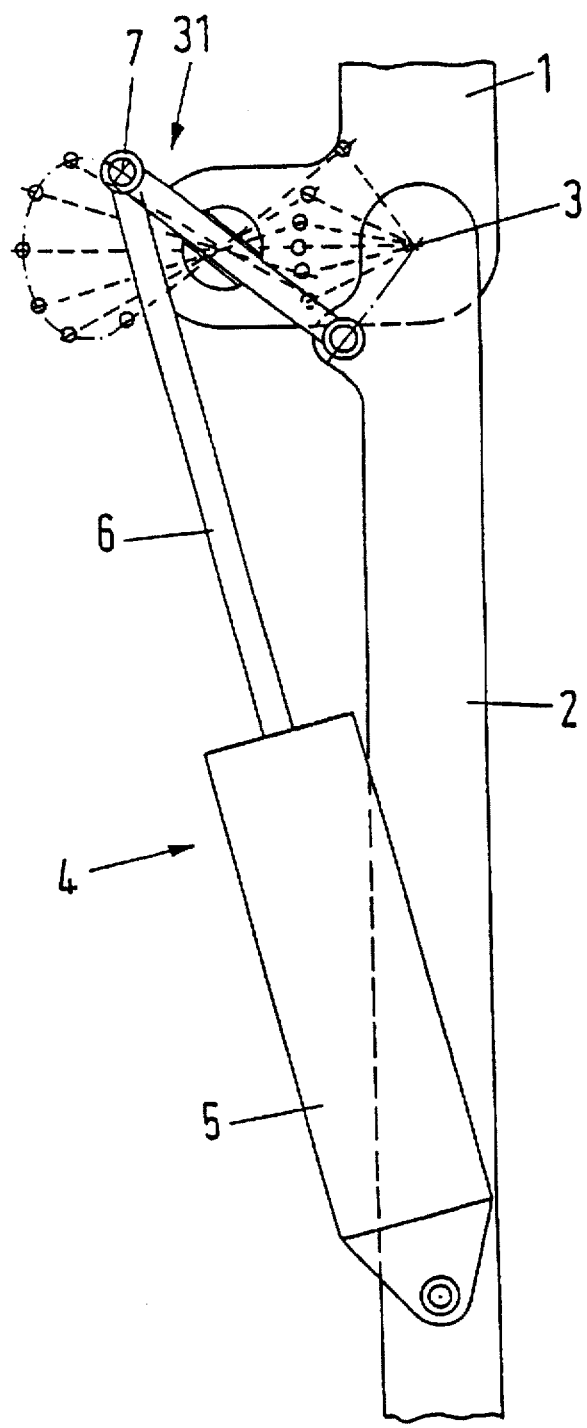
FIG. 11—an illustration as in FIG. 10 of an upper articulation of a control element at the bending side, designed as a cylinder with a piston rod in a unicentered hinge joint using a sliding crank assembly with an internal thrust member.

FIG. 11 shows the change in position dependent on joint angle of the upper articulation at the bending side of a control element 4 in a unicentered hinge joint using a sliding crank assembly with an internal thrust member.

Figure 12:
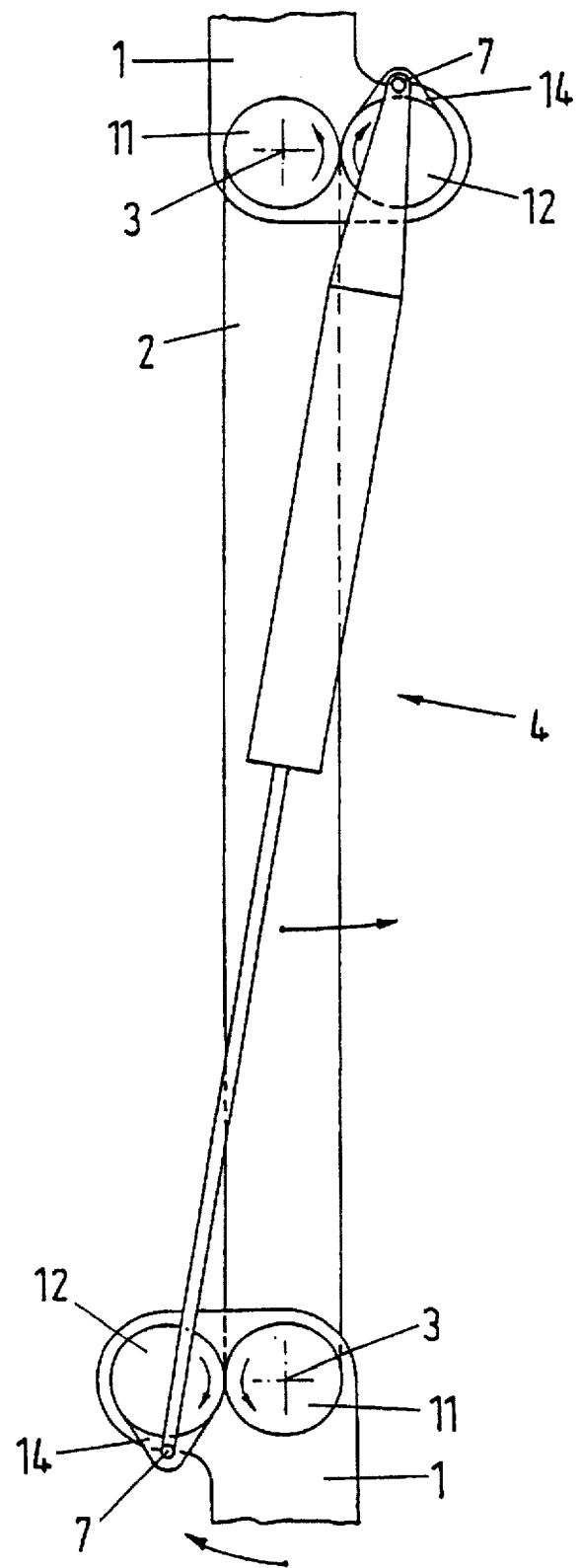
FIG. 12—an illustration as in FIG. 11 of a joint angle-dependent, position-changing articulation of a control element on the stretching side, designed as a cylinder with a piston rod for two unicentered hinge joints using two single-stage spur gear drives.

FIG. 12 shows an articulation, with both ends changing position depending on the joint angle, of a control element 4 designed as a cylinder 5 with piston rod 6 for two unicentered joints using two single-stage spur gear drives.

Figure 13:
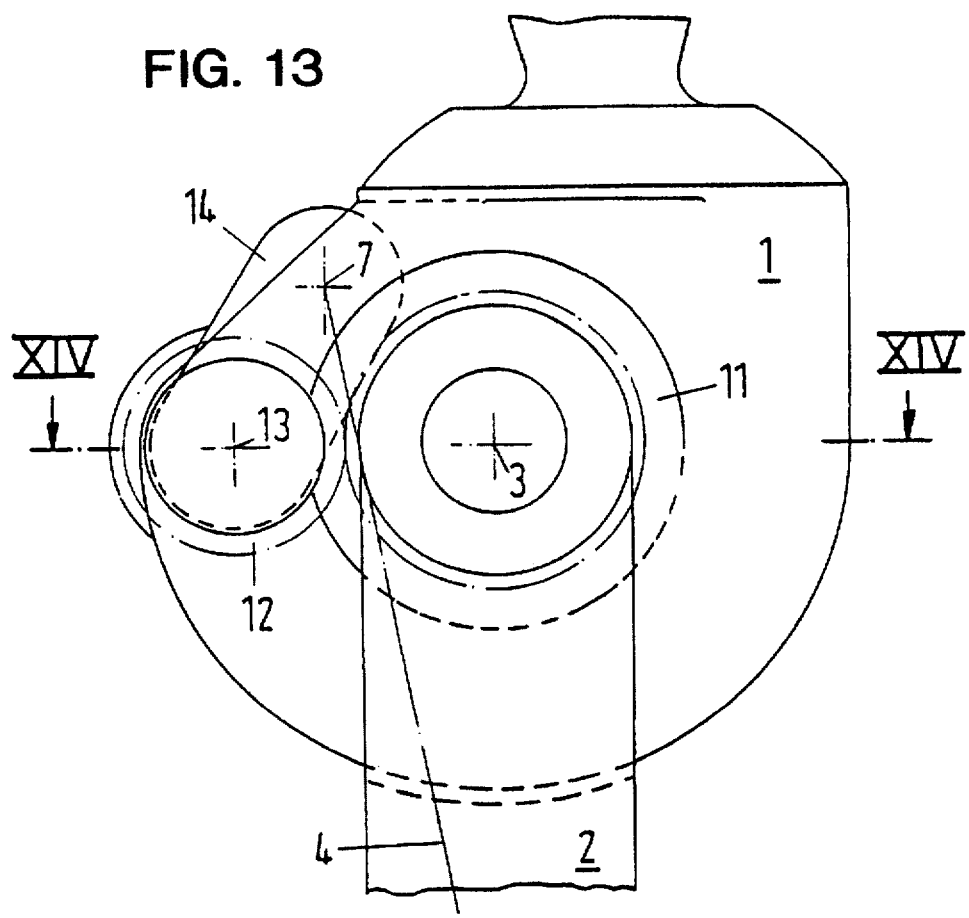
FIG. 13—a top view of a unicentered prosthetic knee joint with joint angle-dependent change of position of the upper articulation of a not further illustrated control element at the bending side using a single-stage spur gear drive.
Figure 14:
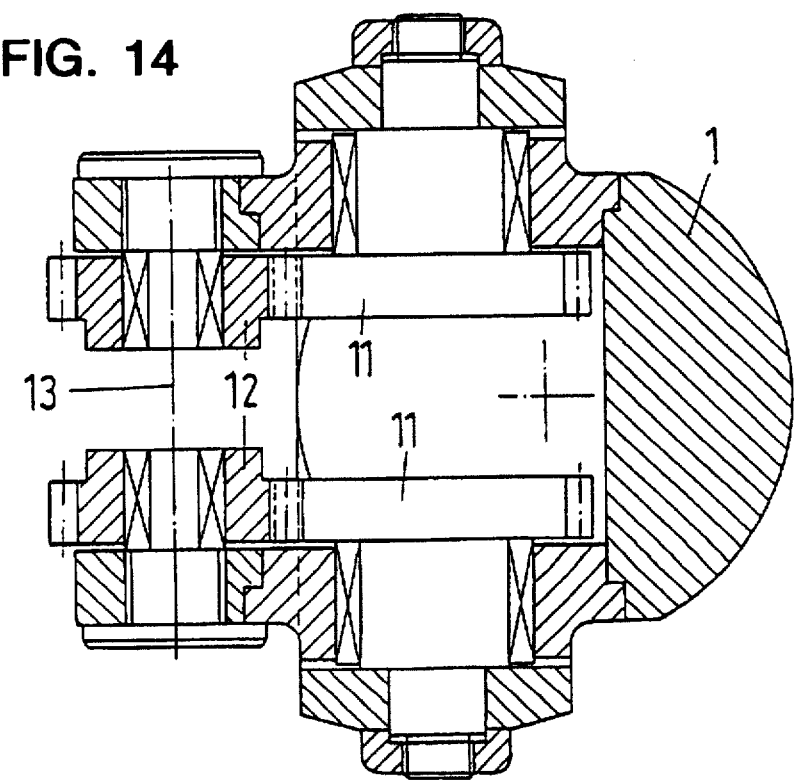
FIG. 14—a section through line XIV—XIV in FIG. 13.

FIGS. 13 and 14 show a unicentered prosthetic knee joint with an upper articulation 7 at the bending side, whose change in position dependent on joint angle, which is part of a control element 4 not illustrated in further detail, using a single-stage spur gear drive. In this case, the lower joint component 2 is connected to the first spur gear 11 mounted on the pivot 3, in such a way that, in the position illustrated, when a bending movement of the joint starts from the stretching position, the spur gear is rotated clockwise by the pivoting of the lower joint component 2, and in turn rotates the second spur gear 12, which meshes with the first gear, in a counter-clockwise direction around its pivot 13 mounted on the bending side of the joint behind its pivot 3. Along with the second spur gear 12, its lever arm 14 and the upper hinge point 7 located on it are rotated. Thereby is the ratio of the pitch diameter of the gear sets formed by the two spur gears 11, 12 selected in such a way that the action reversal occurs in control element 4 at a joint bend angle of 90°.

Figure 16:
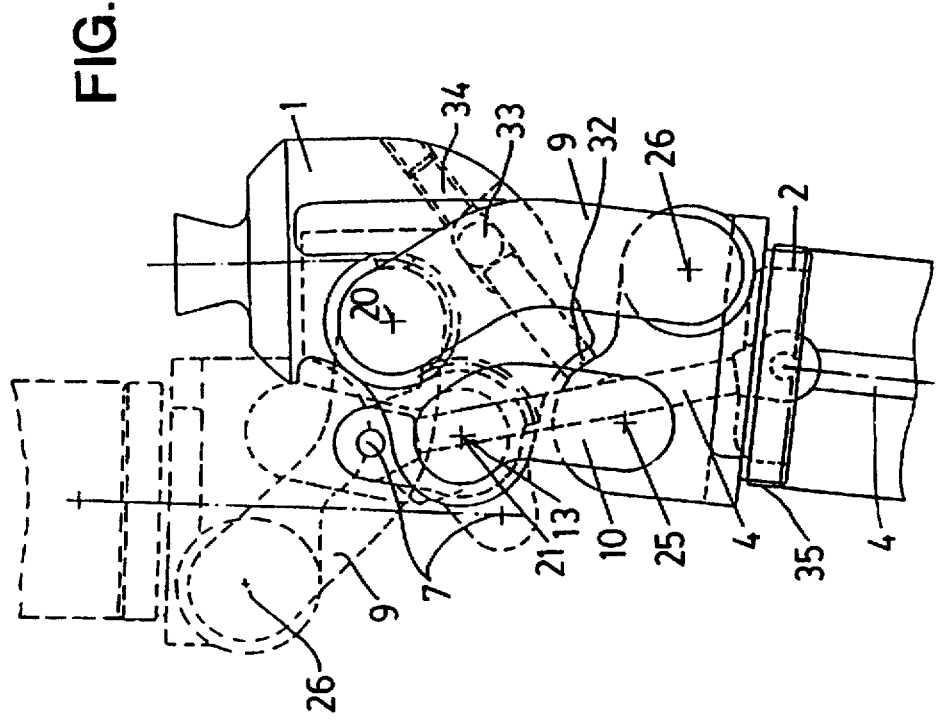
FIG. 16—a top view of the knee joint in FIG. 15.
Figure 15:
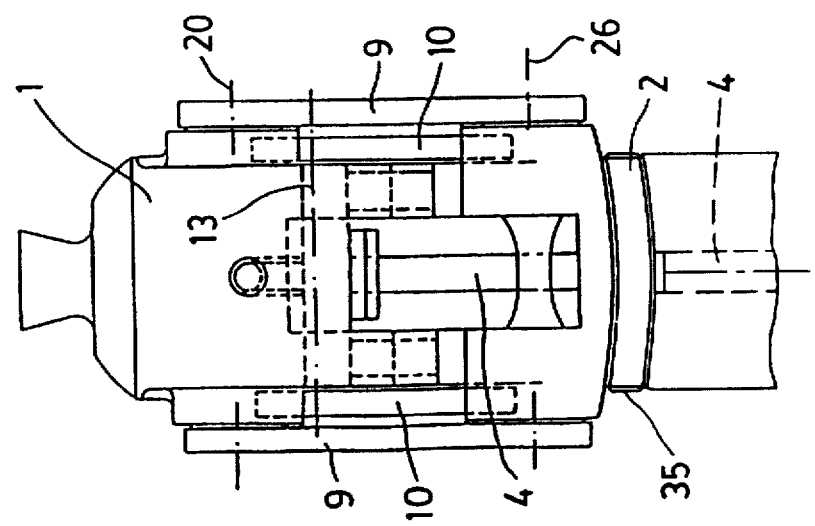
FIG. 15—a side view of a polycentered prosthetic knee joint with joint angle-dependent change of position of the upper articulation of a connecting rod of a not further illustrated control element at the stretching side, using a single-stage spur gear drive.
Figure 17:
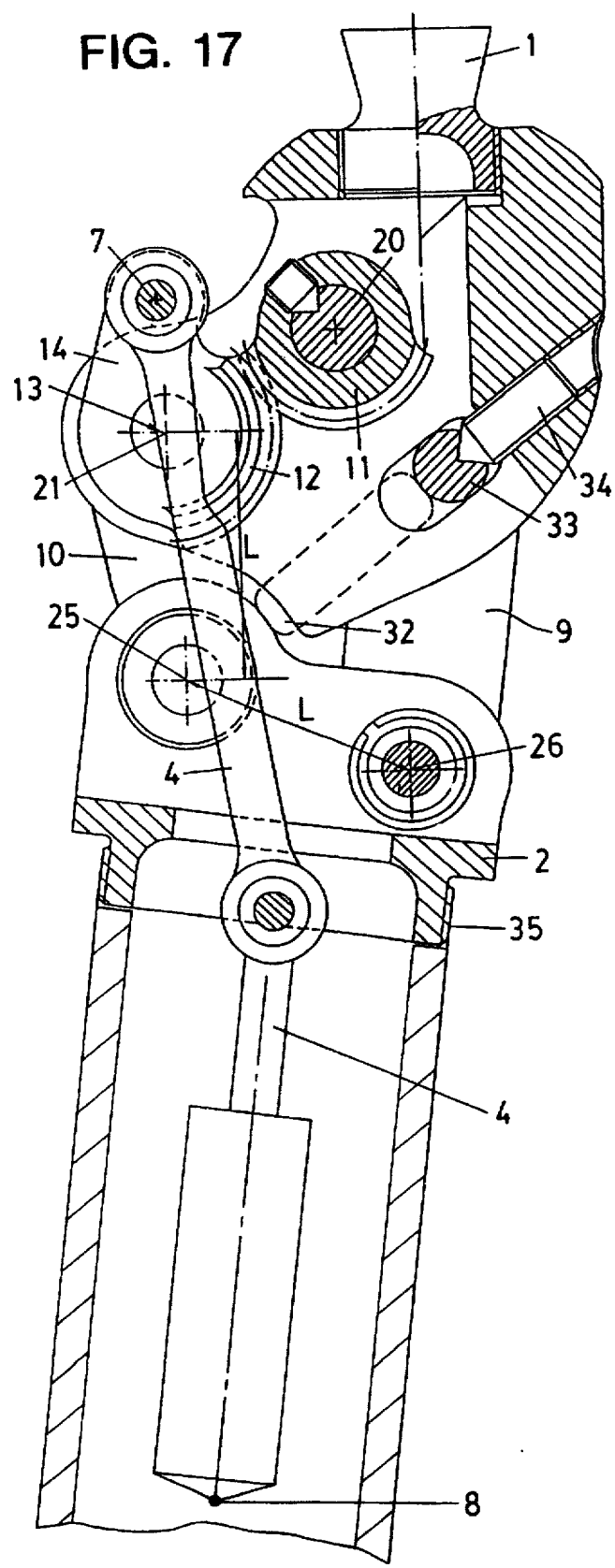
FIG. 17—part of the knee joint of FIG. 16 in a longitudinal section at a larger scale.

In the schematically presented polycentered prosthetic knee joint in FIGS. 15, 16 and 17, a single-stage spur gear drive is also used as the mechanical geared coupling for the change of position of the upper hinge point 7 of control element 4 in upper joint component 1 with the motion of a joint designed as a four-member kinematic chain. Referring to the embodiment shown in FIG. 9, control element 4 is only a part of the entire control element, and accordingly, is adapted to be used with a control element similar to that designated as 29 in FIG. 9. Accordingly, reference is made to the description of the embodiment of FIG. 9 with reference to the additional portion of the control element, referred to therein as control element 29. In this case, the front linkage arm 9 is connected to the first spur gear 11 mounted on the shaft of the upper front articulation 20; this gear is turned in a clockwise direction by the pivoting of the front linkage arm 9 around its upper front articulation 20 when a bending movement of the joint is commenced and the second spur gear 12 meshing with the first is rotated counter-clockwise around its shaft mounted co-axially to the upper rear articulation 21 between upper joint component 1 and the rear linkage arm 10, whereby the lever arm 14 and upper hinge point 7 are moved in the same manner.

The ratio of the pitch diameter of the gear sets formed by the two spur gears 11, 12 selected in such a way that the action reversal occurs in control element 4 at a joint bend angle of 90°.

The greater than average knee bend angle of nearly 180° is particularly advantageous in this embodiment of a polycentered hinge joint. This is made possible by the fact that, with increasing bending of the knee, the upper hinge point 7 pivots away from its stretched position, which is a hindrance for it, along a circular path around its deflection axis towards the rear and thus is not an obstacle.

Construction and functional advantages result from this embodiment when, in the stretched position, the upper pivot 20 of the front linkage arm 9 is positioned over the upper pivot 21 of the rear linkage arm 10 and the lower pivot 26 of the front linkage arm 9 under the lower pivot 25 of the rear linkage arm 10, and when the distance 1 between the two pivots 21, 25 of the rear arm 10 correspond to the distance 1 between the two pivots 25, 26 of the lower joint component 2.

It is further advantageous when the stretched position is defined by an extension stop effective directly between upper joint component 1 and lower joint component 2. In the case of FIG. 17 this stop consists of two bumpers 32, arranged in parallel, which enter into both side walls of the upper joint component, and that are acted upon by an adjustment screw 34 via a common traverse 33. The particular advantage of this design solution may be seen in the fact that when the lower joint component 2 contacts the bumper or bumpers 32, no bending moments are exerted on the front linkage arm 9 in particular. Furthermore, the bumpers can be arranged in upper joint component 1 which is of solid construction.

For the distal joining of the prosthetic components by means of a removable connection, it is advantageous when the lower joint component 2 is fitted with a removable connection in the form of a fine thread 35. In this way, the joint may be combined at the factory with any desired units from the supporting lower thigh structure with an integrated control element.

I claim:

1. A monocentric joint for orthopaedic prostheses and orthoses having an extension side and a flexion side, comprising:

an upper joint component and a lower joint component, said two components being pivotally connected by a hinge joint axis;

said upper joint component includes a first and a second spur gear meshing with each other, the first spur gear being coaxially firmly secured to said hinge joint axis, which axis is firmly secured to said lower joint component, whereas the second spur gear is rotatably mounted on a rotary pivot fixed to said upper joint component and is connected with a crank lever;

a control element having a first and a second end with a variable distance therebetween, the first end being hinged to said crank arm via a first control hinge point, the second being associated with the lower joint component spaced from said hinge joint axis; and upon joint movement, said first control hinge point automatically changes its location relative to the upper joint component, wherein this change in location is performed as a constrained motion by means of a positive coupling with the lower joint component, which coupling is defined by said meshed spur gears.

2. A joint for orthopaedic prostheses and orthoses having an extension side and a flexion side, comprising:

a four-member kinematic link chain defined by an upper joint component and a lower joint component, said two components being coupled on the extension side by an extension side linkage arm and on the flexion side by a flexion side linkage arm via upper hinge joint axes and lower hinge joint axes;

said upper joint component includes a first and a second spur gear meshing with each other, the first spur gear, being coaxially with the upper extension side hinge joint axis, is fixed to the extension side linkage arm, whereas the second spur gear is rotatably mounted on the upper flexion side hinge joint axis and is connected with a crank lever;

a control element having a first and a second end with a variable distance therebetween, the first end being hinged to said crank arm via a first control hinge point, the second end being associated with the lower joint component spaced from the lower hinge joint axes; and upon joint movement, said first control hinge point automatically changes its location relative to the upper joint component, wherein this change in location is performed as a constrained motion by means of a positive coupling with the extension side linkage arm, which coupling is defined by said meshed spur gears.

3. The joint according to claim 2, wherein said first and second spur gears have pitched diameters selected to cause reverse action of said control element to occur at a joint bend angle between said upper and lower joint components of 90°.

4. The joint according to claim 2, wherein said joint exhibits a stretched position and wherein at said stretched position, the upper extension side hinge joint axis is positioned above the upper flexion side hinge joint axis, and the lower extension side hinge joint axis is positioned below the lower flexion side hinge joint axis.

5. The joint according to claim 2, wherein the distance (L) between the upper flexion side hinge joint axis and the lower flexion side hinge joint axis is substantially equal to the distance between the two lower hinge joint axes.

6. The joint according to claim 2, wherein said joint exhibits a stretched position, which position is defined by an extension stop acting directly between said upper joint component and said lower joint component.

* * * * *